United States Patent [19]
Robotti et al.

[11] Patent Number: 5,580,434
[45] Date of Patent: Dec. 3, 1996

[54] INTERFACE APPARATUS FOR CAPILLARY ELECTROPHORESIS TO A MATRIX-ASSISTED-LASER-DESORPTION-IONIZATION MASS SPECTROMETER

[75] Inventors: Karla M. Robotti, Foster City; Joel Myerson, Berkeley, both of Calif.

[73] Assignee: Hewlett-Packard Company, Palo Alto, Calif.

[21] Appl. No.: 609,261

[22] Filed: Feb. 29, 1996

[51] Int. Cl.$^6$ .......................... G01N 27/26; G01N 27/447
[52] U.S. Cl. .......................... 204/451; 204/452; 204/601; 204/603; 250/288
[58] Field of Search .................................... 204/603, 452, 204/601, 451; 250/288

[56] References Cited

U.S. PATENT DOCUMENTS

| | | | |
|---|---|---|---|
| 4,631,120 | 12/1986 | Pohl | 204/465 |
| 4,631,122 | 12/1986 | Pohl | 204/614 |
| 4,735,697 | 4/1988 | Burton | 204/467 X |
| 5,126,025 | 6/1992 | Carson et al. | 204/451 |
| 5,171,989 | 12/1992 | Williams et al. | 250/288 |
| 5,443,727 | 8/1995 | Gagnon | 210/490 |

FOREIGN PATENT DOCUMENTS

| | | |
|---|---|---|
| 475164 | 3/1992 | European Pat. Off. . |
| 477541 | 4/1992 | European Pat. Off. . |
| 617048 | 9/1994 | European Pat. Off. . |

OTHER PUBLICATIONS

Tomonori Konse et al, "Blotting Membrane Microprepration in Capillary Electrophoresis to Evaluate Enzyme Purity and Activity" Analytical Biochemistry 214 (1993) 179–181 No month available.

Hollis J. Boss et al, "Multiple Sequential Fraction Collection of Peptides and Glycopeptides by High-Performance Capillary Electrophoresis" Analytical Biochemistry 230 (1995) 123–129 No month available.

Jianyi Cai & Jack Henion, "Capillary electrophoresis–mass spectrometry" Journal of Chromatography A, 703, (1995) 667–692 no month available.

Yung–Fong Cheng et al "Membrane fraction collection for capillary electrophoresis" Journal of Chromatography 608 (1992) 109–116.

Kjell–Ove Eriksson et al, "Preparative Capillary Electrophoresis Based on Adsorption of the Solutes (Proteins) onto a Moving Blotting Membrane as They Migrate out of the Capillary" Analytical Biochemistry, 201 (Mar. 1992) 211–215.

(List continued on next page.)

*Primary Examiner*—Kathryn Gorgos
*Assistant Examiner*—John S. Starsiak, Jr.

[57] ABSTRACT

An apparatus for collecting samples from capillary electrophoresis (CE) for matrix-assisted laser desorption ionization (MALDI) mass spectrometry (MS) is disclosed. The apparatus has a capillary, a metallic support, a porous member, and a power supply for applying an electrical potential between the porous member and an inlet end of the capillary to drive the sample through the capillary during CE. The capillary transmits a sample from the inlet end to the exit end during capillary electrophoresis. The metallic support supports the porous membrane such that the porous membrane contacts the capillary exit end during CE. The metallic support (with the porous membrane) is suitable for placing in a mass spectrometer to act as a repeller for MALDI. The porous member has at least a portion thereof that is generally concentric with the capillary exit end and contacts the porous membrane during CE. The capillary exit end and the metallic support are adapted to lift the capillary exit end from the porous membrane and reposition it on the porous membrane at a different location to deposit noncontinuously different fractions of the sample exiting the capillary on the porous membrane. When an electrically conducting liquid is present in the porous member, it provides electrical communication between the capillary exit end and the power supply.

19 Claims, 8 Drawing Sheets

OTHER PUBLICATIONS

William J. Warren et al, "Protein Immunodetection Using Capillary Electrophoresis with Membrane Fraction Collection" LC–GC, vol. 12, No. 1, (Jan. 1994) 22,24 & 26–28.

Jonathan V. Sweedler et al "Novel Detection Schemes for the Trace Analysis of Amino Acids and Peptides Using Capillary Electrophoresis" J. Microcolumn Separations, vol. 5, No. 5 (1993) 403–412 No month available.

Michael Albin et al, "The Use of Capillary Electrophoresis in a Micropreprative Mode: Methods and Applications" Analytical Biochemistry 206 (1992) 382–388 No month available.

John A. Castoro et al, "Matrix–Assisted Laser Desorption/Ionization of Capillary Electrophoresis Effluents by Fourier Transform Mass Spectrometry" J. Am. Chem. Soc. 114 (1992) 7571–7572 no month available.

Wolfgang Weinmann et al, "Capillary electrophoresis–matrix assisted laser–desorption ionization mass–spectrometry of proteins" Journal of Chromatography A, 680 (1994) 353–361 no month available.

James A. Blackledge, et al., "Polyethylene Membrane as a Sample Support for Direct Matrix–Assisted Laser Desorption/Ionization Mass Spectometric Analysis of High Mass Proteins", Analytical Chemistry, vol. 67, No. 5, Mar. 1, 1995, pp. 843–848.

W. M. Bodnar, et al., "Analysis of Blotted Peptides and Proteins by MALDI TOF Mass Spectrometry", 42nd ASMS Conference on Mass Spectrometry, p. 683 No date available.

Jeff D. Bryant, et al., "Post–Capillary Immobilon™–P Membrane Fraction Collection for Capillary Electrophoresis", Biotechniques, vol. 14, No. 1 (1993), pp. 51–55 No month available.

Brian T. Chait, et al., "Weighing Naked Proteins: Practical, High–Accuracy Mass Measurement of Peptides and Proteins", Science, vol. 257, 25 Sep. 1992, pp. 1885–1894.

Lynn Chakel, "A Matrix–Assisted Laser Desorption/Ionization Time–of–Flight Mass Spectrometer", American Laboratory No date available.

Rick W. Chiu, et al., "Coaxial Capillary and Conductive Capillary Interfaces for Collection of Fractions Isolated by Capillary Electophoresis", Analytical Chemistry, vol. 67, No. 22, Nov. 15, 1995, pp. 4190–4196.

Franz Hillenkamp, et al., "Matrix–Assisted Laser Desorption/Ionization Mass Spectrometry of Biopolymers", Analytical Chemistry, vol. 63, No. 24, Dec. 15, 1991, pp. 1193–1203.

Klaus Klarskov, et al., "Plasma Desorption Mass Spectrometry of Proteins Transferred from Gels After Sodium Dodecyl Sulphate–Polyacrylamide Gel Elecrophoresis", Biological Mass Spectrometry, vol. 22, (1993) pp. 433–440 No month available.

K. K. Mock, et al., "Sample Immobilization Protocols for Matrix–Assisted Laser–Desorption Mass Spectrometry", Rapid Communications in Mass Spectrometry, vol. 6, (1992) pp. 233–238 No month available.

Kerstin Strupat, et al. "Matrix–Assisted Laser Desorption Ionization Mass Spectrometry of Proteins Electroblotted After Polyacrylamide Gel Electrophoresis", Analytical Chemistry, vol. 66, No. 4, Feb. 15, 1994, 66, pp. 464–470.

Martha M. Vestling, et al., "Poly (vinylidene difluoride) Membranes as the Interface Between Laser Desorption Mass Spectrometry, Gel Electrophoresis, and In Situ Proteolysis", Anal. Chem. 1994, 66, pp. 471–477 No month available.

Martha M. Vestling, et al. "Polyvinylidene Difluoride (PVDF): An Interferen for Gel Electrophoresis Matrix–Assisted Laser Desorption/Ionization Mass Spectrometry", Biochemical Application of Mass Spectrometry, May 1994, vol. 22, No. 2, pp. 547–551.

Ole Vorm, et al., "Improved Resolution and Very High Sensitivity in MALDI TOF of Matrix Surfaces Made by Fast Evaporation", Analytical Chemistry, vol. 66, No. 19, Oct. 1, 1994, pp. 3281–3287.

Kathleen L. Walker, et al., "Off–Line Coupling Electrophoresis and Matrix–Assisted Laser Desorption/Ionization Time–of–Flight Mass Spectrometry", Anal. Chem. 1995, 67, pp. 4197–4204 No month available.

Scot R. Weinberger, "The Laser Desorption–Ionization MassMonitor: A Powerful Analytical Tool for Life Science Investigations", Reprinted from American Laboratory, Mar. 1992.

E. J. Zaluzec, et al., "Direct Matrix–Assisted Laser Desorption Ionization Mass Spectrometric Analysis of Protein Immobilized on Nylon–Based Membranes", American Society for Mass Spectrometry 1994, 5. pp. 230–237 No month available.

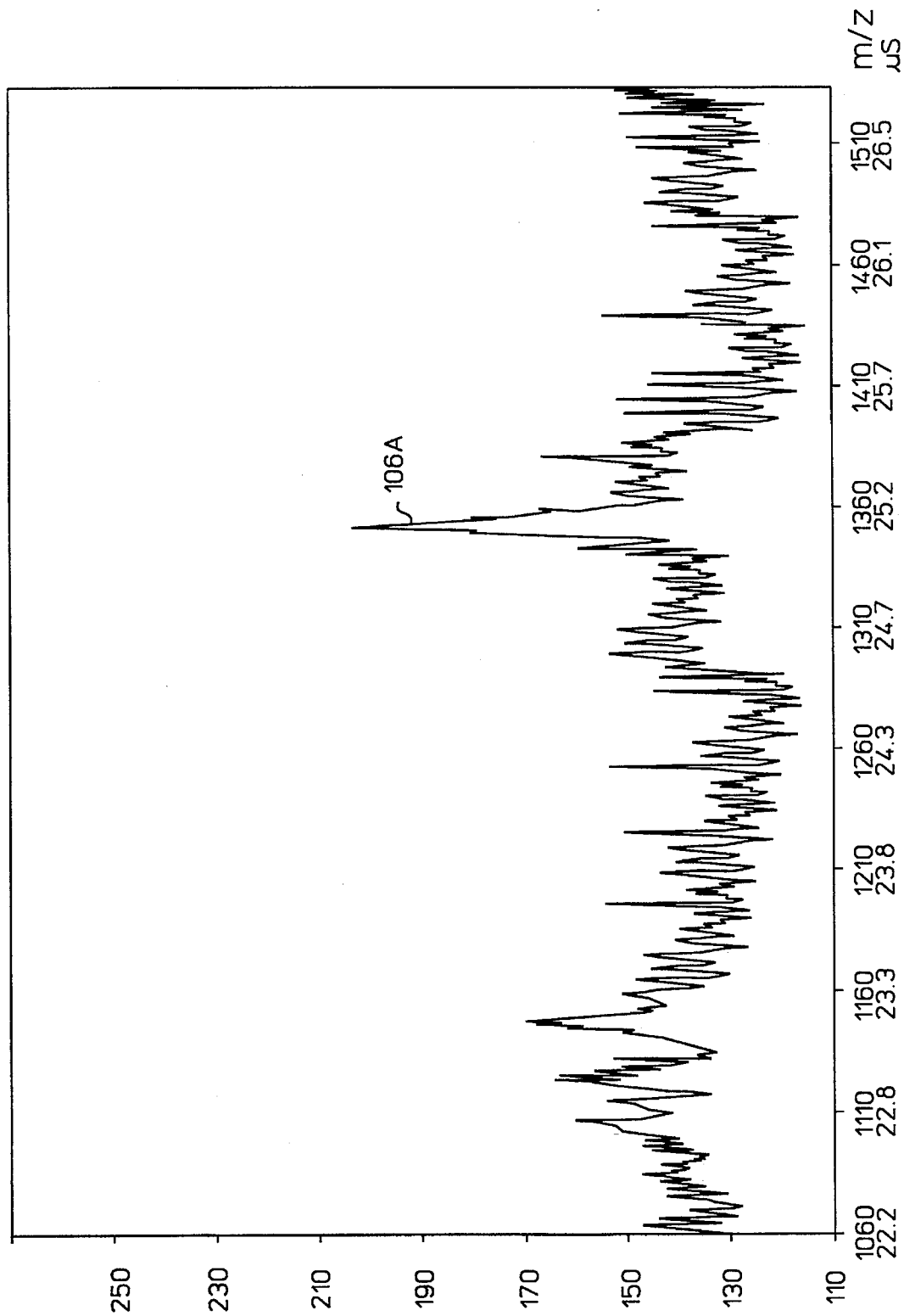

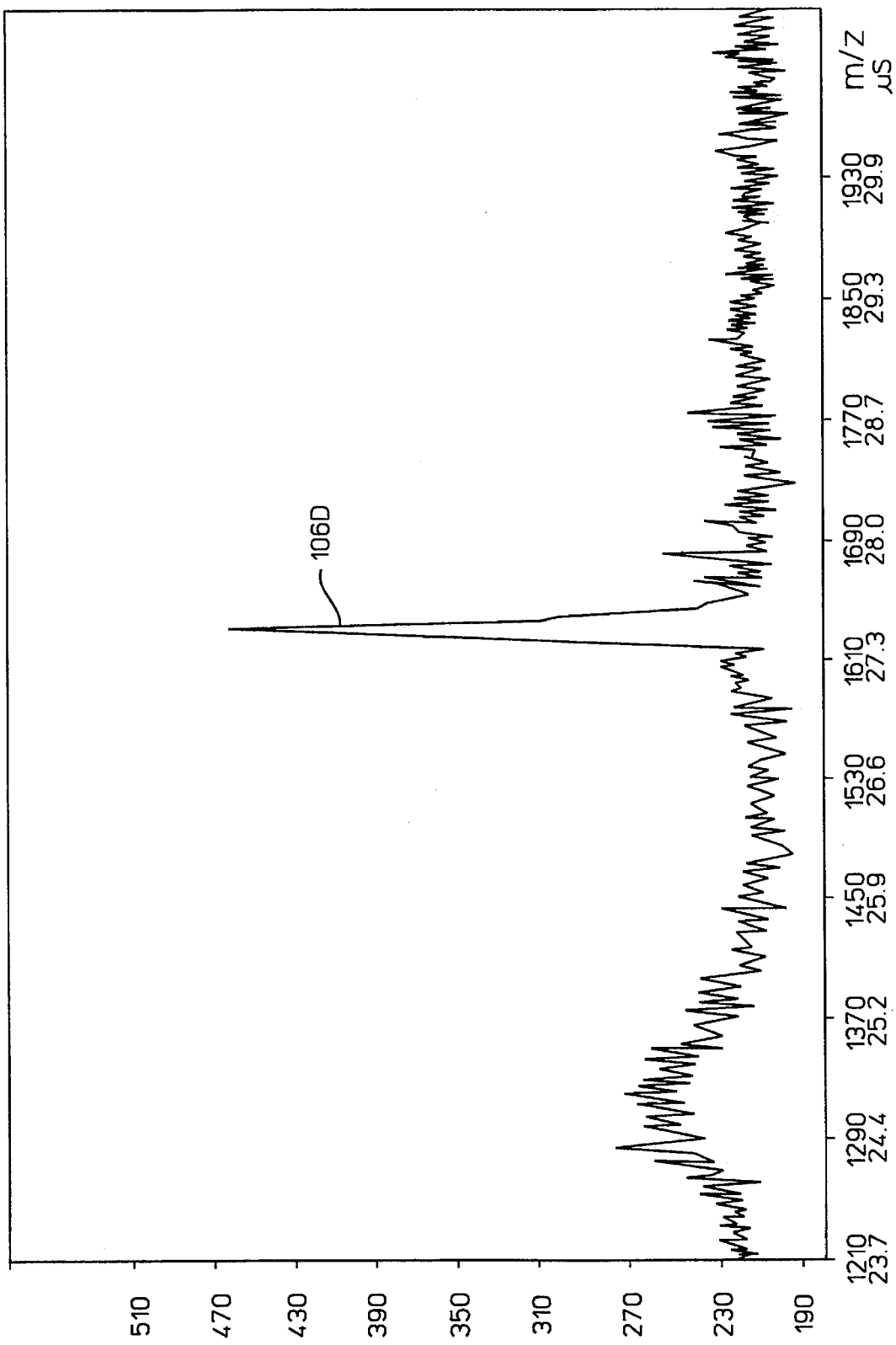

INTERFACE APPARATUS FOR CAPILLARY ELECTROPHORESIS TO A MATRIX-ASSISTED-LASER-DESORPTION-IONIZATION MASS SPECTROMETER

FIELD OF THE INVENTION

The present invention relates to apparatuses and methods for collecting samples, and more particularly, to apparatuses and methods for collecting fractions from capillary electrophoresis for matrix-assisted laser desorption ionization (MALDI) time of flight (TOF) mass spectrometry (MS).

BACKGROUND

Recently, matrix-assisted laser desorption ionization (MALDI) has been gaining acceptance as a way to ionize analytes for time of flight (TOF) mass spectrometry (MS), especially for analysis of large molecules such as proteins. Generally, a matrix material (e.g., 2,5-dihydroxybenzoic acid, nicotinic acid, cinnamic acid derivatives such as sinapinic acid) and analytes are applied to a surface so that crystals of the matrix materials and analyte solids are formed thereon. Typically, laser radiation is used for ionization of the analytes. After ionization, the ions can be separated (and therefore identified) according to their mass-to-charge ratios in mass spectrometry.

In analyzing large molecules, such as proteins, peptides, and nucleic acids, gel electrophoresis (GE) is a routinely used technique. MS is considered to be very useful for identifying analytes separated in GE. For interfacing gel electrophoresis with MS, membranes have been evaluated as sample supports for MALDI-MS (e.g., Blackledge et al., *Anal. Chem.*, 1995, 67, 843–848; Zaluzec et al., *J. Am. Soc. Mass. Spectrom.*, 1994, 5, 230–237; Vesting et al., 1994, *Anal. Chem.*, 66. 471–477). To take advantage of this technology, analytical samples are placed on a repeller in the mass spectrometer to be ionized and repelled. However, some analytical samples are not amenable to be readily used for MALDI-MS. The process of transferring analytical samples from other analytical apparatuses to MALDI-MS can be labor-intensive (e.g., transferring protein from a gel to a membrane by electroblotting). Even worse, the samples may not contain a high enough concentration of analytes.

Capillary electrophoresis (CE) has also emerged as a powerful tool for efficient separation of analytes in an aqueous solution. CE analysis is conducted in a capillary that is immersed in an electrolyte. When an analytical sample is introduced into the capillary and an electrical potential is applied to the two ends of the capillary, the resulting electric field causes analytes to migrate along the capillary, as well as draws the electrolyte through the capillary. The analytes move from one end of the capillary to the other end, each at a rate dependent on its electrophoretic mobility and the rate of fluid flow in the capillary. To collect samples of analytes exiting a CE system for MALDI-MS, the fractions exiting the CE capillary need to be collected and applied on a substrate that is suitable for supporting the ionization of analytes in the MS.

Carson et al. (U.S. Pat. No. 5,126,025, also *BioTechniques*, 1993, 14(1):51–55) describes an apparatus for collecting fractions from capillary electrophoresis on a membrane. The apparatus is described as having a capillary tube, a porous layer containing an electrolyte, a first electrode adjacent the entrance end of the capillary, and a second electrode in electrical contact with the porous layer. A liquid absorbent layer or a containerful of liquid is in contact with the porous layer to supply it with the electrolyte (to wet the porous layer). There is no indication that this system can be used to collect samples for MALDI-MS analysis. The electrolyte (in constant contact with the porous layer and being supplied continuously by the absorbent or container) will cause diffusion and spreading of the analytes exiting the capillary on the porous layer, thereby lowering the concentration of analytes and resulting in analyte-containing spots or streaks with large surface areas. This will result in less accuracy if used in MALDI-MS analysis of the unknown sample. What is needed is an apparatus and method for collecting fractions from samples eluting from a capillary in CE to result in analytecontaining spots of higher concentrations and smaller surface areas.

SUMMARY

The present invention provides an apparatus for collecting samples from capillary electrophoresis (CE) for matrix-assisted laser desorption ionization (MALDI) time of flight (TOF) mass spectrometry (MS). The apparatus includes a capillary for conducting a sample during capillary electrophoresis; a metallic support, a porous member (e.g., a wick), and a power supply. The capillary has an inlet end and an exit end. The metallic support is used for supporting a porous membrane (e.g., a polymeric membrane) such that the porous membrane contacts the capillary exit end during capillary electrophoresis and is suitable for placement (with the porous membrane on it) in a mass spectrometer to act as a repeller for MALDI. At least a portion of the porous member is generally concentric with the capillary exit end (e.g., the exit end is inserted into a cylindrical wick). The porous member substantially contacts the porous membrane to deposit fluid fractions during capillary electrophoresis. The capillary exit end and the metallic support are adapted to lift the capillary exit end from the porous membrane and reposition it on the porous membrane at a different location. In this way, the capillary can deposit noncontinuously on the porous membrane different fractions of the sample exiting the capillary (although the separation in the capillary by CE can be continuous). An electrical potential is applied by the power supply between the porous member and the inlet end of the capillary. This electrical potential drives the sample through the capillary during capillary electrophoresis when an electrically conducting liquid wets the porous member to provide electrical communication between the capillary exit end and the power supply.

The apparatus of the present invention can be used advantageously to interface CE and MS. Because the capillary exit end and the porous member are in contact with the porous membrane intermittently and the area of contact is very small, the fluid fractions that are deposited on the membrane will not spread appreciably due to diffusion, thereby maintaining a high concentration and small spot size, making possible better laser desorption of analytes. Furthermore, in the embodiment wherein the exit end of the capillary is inserted into the porous member, the porous member and the capillary exit end can be lifted and moved as a unit. This greatly simplifies the mechanical complexity that is required to move the porous member and capillary exit end separately and align them to ensure good electrical connection and fluid communication. Also, having both the exit end of the capillary and the porous member on the same side of the porous membrane (and therefore of the metallic support) is also advantageous. The other side of the metallic support is free to be connected to mechanisms (such as gears for translational movement) for positioning the metallic support relative to the capillary and the porous member.

Additionally, the cumbersome prior art procedure of transferring electrophoresis analyte samples to a MS probe prior to MS analysis is greatly simplified. The electrically conducting support (e.g., a metallic plate or grid) is adapted to be placed in the ionization chamber in a mass spectrometer and can act as a repeller in MS. Before MALDI-MS analysis is performed, all that is required is taking the metallic support (with the solid MALDI matrix and the analytes on the porous membrane, which in turn remains secured to the support) and placing it inside the mass spectrometer.

BRIEF DESCRIPTION OF THE DRAWINGS

The following figures, which show the embodiments of the present invention, are included to better illustrate the interface apparatus of the present invention. In these figures, like numerals represent like features in the several views and the drawings are not to scale so as to better illustrate features.

FIG. 6A shows the result of a mass spectrum showing the Substance P peak of the 9-component mixture, obtained by analyzing a CE fraction using the interfacing apparatus according to the present invention.

FIG. 6D shows the result of mass spectrum showing the Bombesin peak of the 9-component mixture, obtained using the interfacing apparatus according to the present invention.

DETAILED DESCRIPTION OF THE INVENTION

The apparatus and methods of the present invention use discontinuous contact between an outlet end of a capillary in capillary electrophoresis and a substrate (i.e., a porous membrane) to intermitently deposit thereon fractions of a sample being eluted in the capillary electrophoresis.

Apparatus for Collecting Fractions from CE

Figure 1:
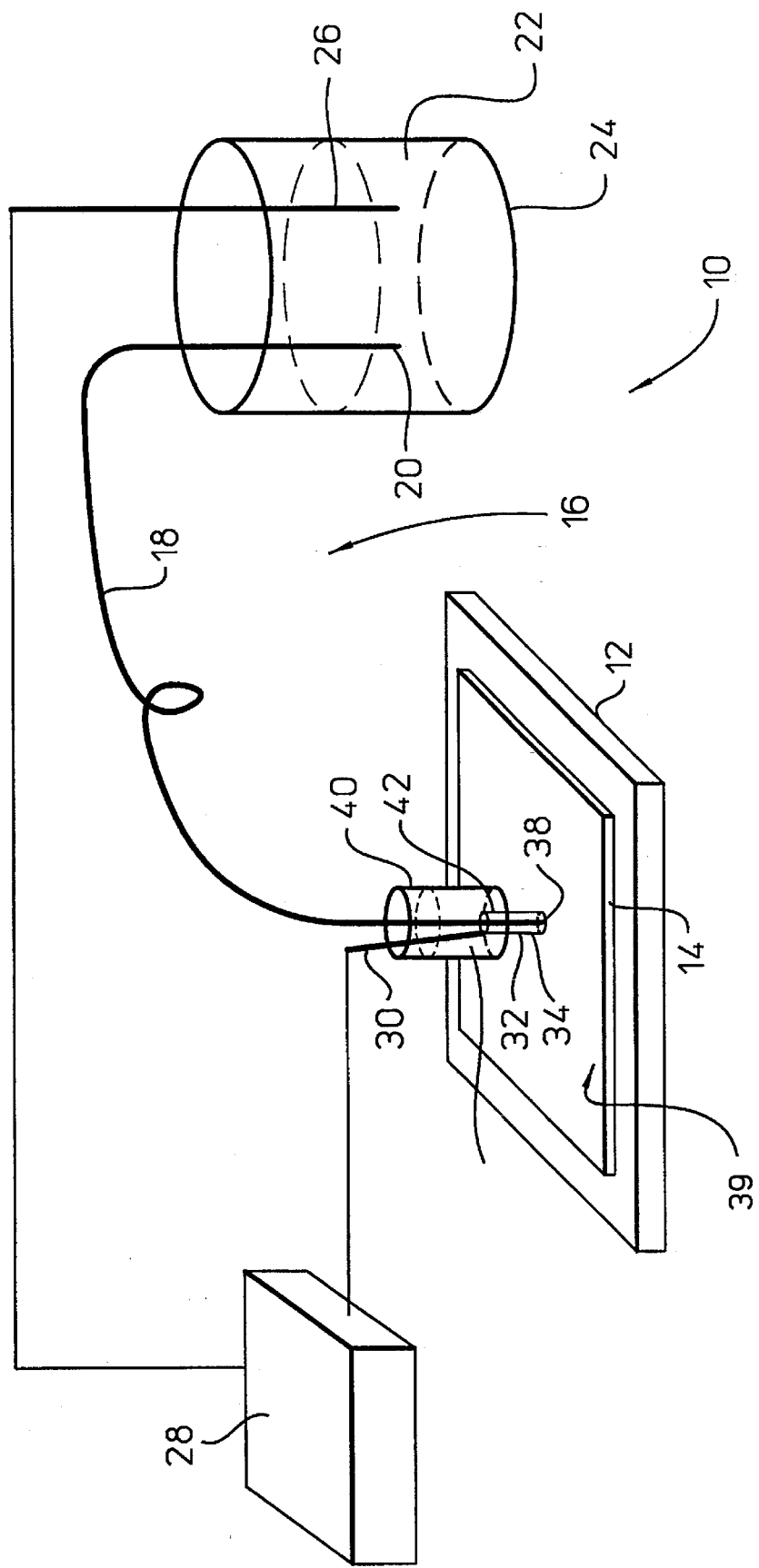
FIG. 1 shows an isometric representation of an embodiment of interfacing apparatus according to the present invention.
Figure 2:
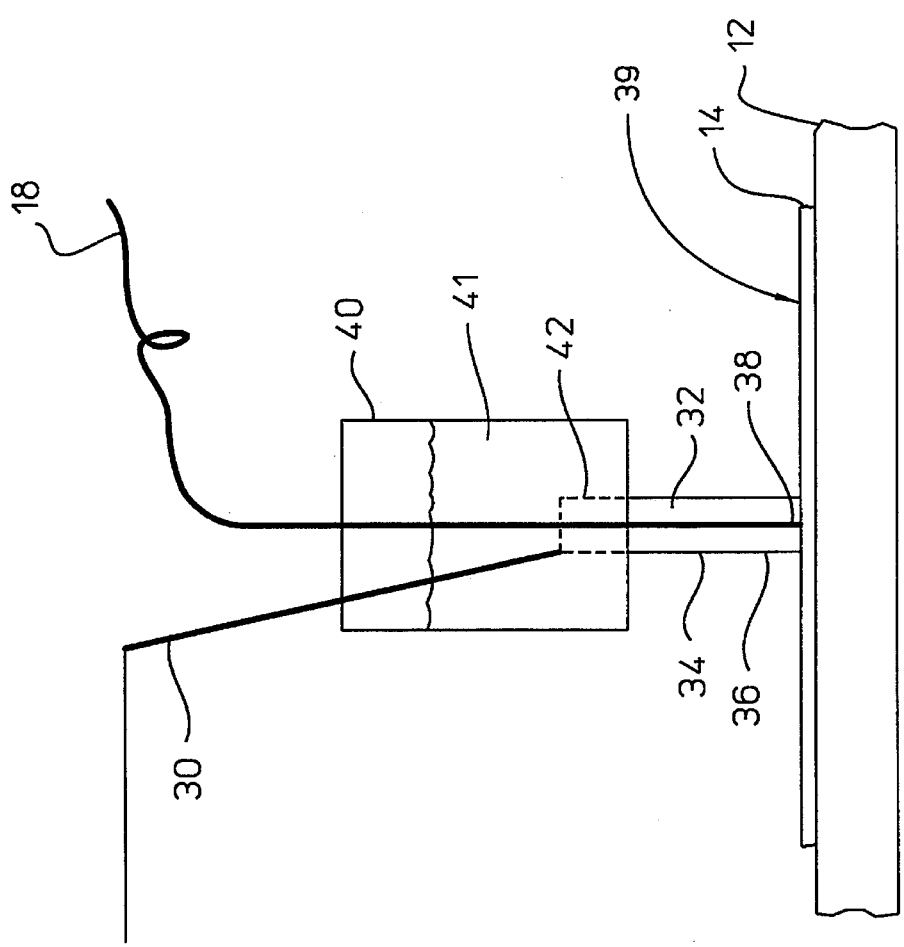
FIG. 2 shows a sectional representation of a portion of the embodiment of interfacing apparatus shown in FIG. 1 according to the present invention.

FIG. 1 shows a preferred embodiment of an apparatus for collecting CE elution fractions according to the present invention. In FIG. 1, the apparatus 10 has a support (or frame) on which a porous membrane 14 (i.e., substrate for the fractions of a CE sample to deposit on) can be secured (or mounted). A capillary electrophoresis (CE) system 16 permits a liquid sample (typically containing one or more analytes) to be analyzed by CE. The CE system 16 has a capillary 18 through which the sample can be eluted during CE analysis. The inlet end 20 of the capillary 18 is dipped in a CE buffer 22 contained in a buffer container 24. A first electrode 26 for applying the electrical potential to the capillary is also dipped in the CE buffer 22. The first electrode 26 is electrically connected to a power supply 28 which supplies the electrical potential for driving the CE. A second electrode 30 is connected to the power supply 28 so that a high electrical potential (e.g. 30 KV) can be applied between the first and the second electrodes 26, 30. The second electrode 30 is in contact with a porous member 32 (e.g., a wick) so that an electrical current can be passed from the second electrode 30 through the porous member 32 when an electrolyte is present therein.

The porous member 32 has a cylindrical portion 34 having an end 36 adapted to be positioned to contact the porous membrane 14. The exit end (outlet end) 38 of the CE capillary 18 is generally concentric with the cylindrical portion 34 of the porous member 32. As shown in FIG. 1, the exit end 38 of the capillary 18 is inserted through the porous member 32 (therefore through the cylindrical portion 34) so that the tip of the exit end 38 of the capillary 18 is about flush with the tip of the cylindrical end 36 of the porous member 32. In this way, when the exit end 38 of the capillary 18 and the cylindrical end 36 of the porous member 32 are placed to contact the porous membrane 14 on its surface 39, eluted liquid from the capillary can be deposited on the porous membrane. Also, liquid can be transferred from the tip of the exit end 38 of the capillary to the cylindrical end 36 of the porous member 32 during electrophoresis so that the electrical circuit is complete for current to pass through the porous member to drive the CE. It is understood that the tip of the exit end of the capillary 18 can be beneath or can extend slightly out of the surface of the cylindrical end 36 of the porous member 32, as long as liquid fractions can pass from the capillary exit end 38 to the porous member 32 and can be deposited on the porous membrane 14. Although because of the ease of implementation it is preferred that the tip of the capillary exit end 38 intermittently contacts the porous membrane 14 physically, the tip of the exit end 38 can be proximate to but not touching the porous membrane 14, as long as the proximity is adequate for the liquid exiting the exit end 38 to deposit on the porous membrane 14. Furthermore, although because of the ease of construction and the even distribution of fluid it is preferred that the porous member 14 is cylindrical, in fact the porous member can have a variety of shape as long as it has a portion that provides a way for the fluid exiting the capillary to communicate with the reservoir. That portion is preferably cylindrical and concentric with the capillary exit end 38. However, it need not be cylindrical and the capillary exit end 38 can be off center on it.

A reservoir 40 encircles (or encloses) a portion (the upper portion) of the porous member 32 distal to the tip of the exit end 38 of the capillary 18. An electrolyte 41 (which can be the same buffer that is in the container 22) in the reservoir 40 is in contact with the upper portion 42 (for purpose of wetting) of the porous member 32 to provide a path for the liquid in the capillary 18 to have electrical communication with the second electrode 30.

The support (or frame) 12 is made of an electrically conducting material (such as metal) so that it (with the porous membrane secured thereto) can be placed inside the ionization chamber in a mass spectrometer. When an appropriate voltage is applied to the support in the mass spectrometer and an analyte on the porous membrane is ionized (e.g., as by laser irradiation), the support acts as a repeller for repelling ionized analyte. The support can be a metallic plate. In another embodiment, the support 12 can be a metallic gridlike structure. It is contemplated that a metallic support having other generally planar shapes (e.g., a mesh appearance) can also be used.

The apparatus 10 uses noncontinuous contact (i.e. intermittently depositing different fractions exiting the capillary) to place fractions of the sample on the porous membrane 14. In operation, when a sample is being eluted from the capillary by CE, liquid continuously exits the exit end 38 of the capillary 18. When the tip of the exit end 38 of the capillary 18, as well as the cylindrical end 36 of the porous member 32, are proximate (in contact or almost in contact) with the porous membrane 14, the liquid exiting the exit end 38 of the capillary comes into contact with the porous membrane. Subsequently, when the exit end 38 of the capillary and the porous member 32 are lifted from the porous membrane 14, some of the material exiting the capillary is deposited on the porous membrane 14. The exit end 38 of the capillary and the porous member 32 can then be positioned at a different location on the porous membrane 14 to deposit another fraction of the material exiting the capillary 18. In this way, by periodically contacting the porous membrane 14 at different locations with the exit end 38 of the capillary 18 and the cylindrical end 36 of the porous member 32, different fractions of the sample being eluted from the capillary can be collected for analysis in a mass spectrometer. Instead of lifting the capillary exit end 38 and the porous member 32 from the porous membrane 14, alternatively, the porous membrane can be moved (e.g., lowered) from the capillary exit end/porous member and repositioned.

The size of the exit end 38 of the capillary 18 and the size of the cylindrical portion 34 of the porous member 32 are selected so that a suitable amount of analyte can be deposited on each location on the porous membrane 14 to enable ionization by MALDI. Generally, the porous member 32 has a cylindrical portion 34 with a diameter of about 1 to about 10 mm, preferably about 2 to 5 mm, and more preferably about 2 mm. With such ranges of sizes, the material deposited on the porous membrane 14 typically has a spot size of about 1 to about 5 mm in diameter, and preferably about 1 to about 2 mm in diameter. It is understood that generally the concentration of the analytes is the highest at the center of the spot (at which the capillary exit end 38 is located).

The material of construction, size, and shape of the porous member 32 is not critical as long as the porous member provides adequate fluid communication between the capillary exit end 38 and the reservoir 40 and enables electrical communication between the capillary exit end and the electrode 30 when an electrolyte is present. For example, although a pore size of about 20 to 40 μm is useful, the porous member can have a different pore size. The size of the porous member can also be different from that previously described. A variety of materials can be used to make the porous member, including, for example, ceramic, glass, and polymeric materials. It is to be understood that a porous member of other size, shape, porosity, and material can be used.

The MALDI matrix can be deposited on the porous membrane 14 prior to or after the deposition of fractions (from CE) on the porous membrane. Methods of depositing an analyte sample on a MALDI matrix on a substrate are known in the art (e.g., Veorm et al., *Anal. Chem.*, 1994, 66, 3281–3287). Likewise, methods of depositing a MALDI matrix on analytes already deposited on a porous membrane are known in the art (e.g. Blackledge et al., *Anal. Chem.*, 1995, 67, 843–848; Zaluzec et al., *J. Am. Soc. Mass. Spectrom.*, 1994, 5, 230–237). These methods can be adapted for application in the present invention.

Many types of porous membranes have been reported as suitable substrates for MALDI for mass spectrometry. Examples include nitrocellulose (Klarskov et al., *Biol. Mass. Spectrom.*, 1993, 22, 433–440); nylon (Zaluzec et al., supra); poly-(vinylidene difluoride) (PVDF) (e.g., Vestling et al., *Biochemical Applications of Mass. Spectrometry*, 1994, 22, 547–551; Blackledge et al., supra); polyethylene (e.g., Blackledge et al., supra), polytetrafluoroethylene (PTFE) (e.g., Bodnar et al., 1994, *Processings of the 42nd ASME Conference on Mass Spectrometry and Allied Topics*, Chicago, IL, May 24–June 3), and siliconized glass fiber membranes.

Preferably, the porous membrane is an organic membrane. More preferably, it is made of olefin; even more preferably, polypropylene or polyethylene. Preferably, the porous membrane is hydrophilic so that it can retain aqueous samples better. The membrane is porous for retaining analytes and the MALDI matrix. Preferably, the pores are about 0.1 to about 20 μm, although other pore sizes can also be used. Porous polymeric membranes are commercially available. For example, nylon porous membranes can be obtained from Anspec, Ann Arbor, MI. Polyethylene membranes and polypropylene membranes can be obtained from 3M Company, St. Paul, Minn. PVDF membranes can be obtained from, e.g., Schleicher & Schuell, Keene, NH (WESTRAN membrane); Millipore, Bedford, Mass. (IMMOBILON-P membrane). PTFE porous membranes can be obtained from, e.g., Norton Performance Plastics (ZITEX membrane). Nitrocellulose and polyamide membranes can be obtained form Sartoris, Gottingen, Germany. Siliconized glass fiber membranes can be obtained from Biometra, Gottingen, Germany. Nitrocellulose porous membranes can be made by electrospraying (which methods are known in the art, e.g., Nielsen et al., 1988, *Biomed. Envron. Mass Spectrom.*, 17, 355).

Methods of making porous polymeric membranes hydrophilic are also known in the art. For example, an organic liquid can be applied on the surface of the polymeric porous membrane to render it more hydrophilic. Examples of applicable organic liquids include methanol, acetone, acetonitrile, and toluene. Such organic solvents can be used to wet the polymeric porous membrane so that the membrane is receptive to an aqueous substance (e.g., fractions eluted from the CE capillary, or MALDI matrix material dissolved in a solvent). A preferred method of imparting hydrophilicity to a membrane is to form a thin film of tactic, hydrophilic poly(vinyl alcohol) on the membrane surface (e.g., as described by Gagnon in U.S. Pat. No. 5,443,727, which method of imparting hydrophilicity is incorporated by reference herein).

Generally, the thickness of the porous membrane is selected to maintain the mechanical integrity during fraction collection and mass spectrometry. For example, the thickness can be about 10 to about 80 μm. Another factor in selecting the thickness of the porous membrane is that during ionization, the ionized analytes should be readily repelled with the application of an electrical potential to the metallic support.

A variety of chemicals can be used as the MALDI matrix, including (but not limited to) nicotinic acid, 2,5-dihydroxybenzoic acid, sinapinic acid, succinic acid, glycerol, α-cyano-4-hydroxycinnamic acid, and 3-hydroxypicolinic acid.

Preferably, the analyte fractions are applied to the porous membrane, dried, and then the MALDI matrix is deposited thereon with up to 6% organic acid (trifluoacetic acid (TFA), formic acid, and the like). If desired (but not necessarily), the dried analyte on the porous membrane can first be washed by immersing in either deionized water or aqueous 0.1% TFA for a few seconds (e.g., about 15–20 seconds) at room temperature and then dried before a solution containing MALDI matrix (e.g., a saturated solution of sinapinic acid in 1:1 acetonitrile/aqueous 0.1% TFA) is applied on the porous membrane and air dried.

Figure 3:
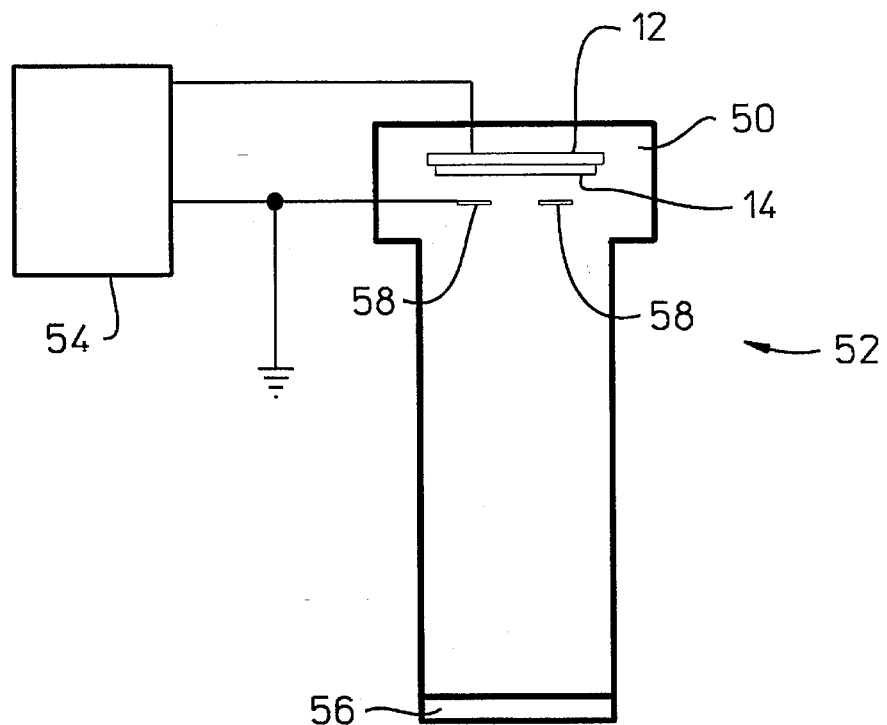
FIG. 3 shows a plan view of a portion of a mass spectrometer for MALDI analysis according to the present invention.

After the analyte fractions and the MALDI matrix have been deposited on the porous membrane, the porous membrane and the metallic support can be taken and placed inside the ionization chamber of a mass spectrometer for MALDI-MS analysis. FIG. 3 illustrates how the MALDI-MS is conducted. The method and equipment for conducting MALDI-MS is known in the art. Briefly stated, after the porous membrane 14 and the metallic support 12 have been positioned in the ionization chamber of a mass spectrometer 52, the ionization chamber 50 is evacuated to result in a vacuum of a magnitude suitable for MALDI. The metallic support is electrically connected to a voltage supply 54, which provides the electrical potential for driving ions (resulting from ionization of analytes on the porous membrane 14) towards a detector 56. Ground electrodes 58 connected to the ground potential of the power supply 54 provides a gate for ions to pass through from the porous membrane 14 towards the detector 56. Ionization of the analytes deposited on the porous membrane 14 can be effected by a laser beam. Methods for irradiating samples with laser and repelling the matrix and the resulting ions are known in the art.

Figure 4:
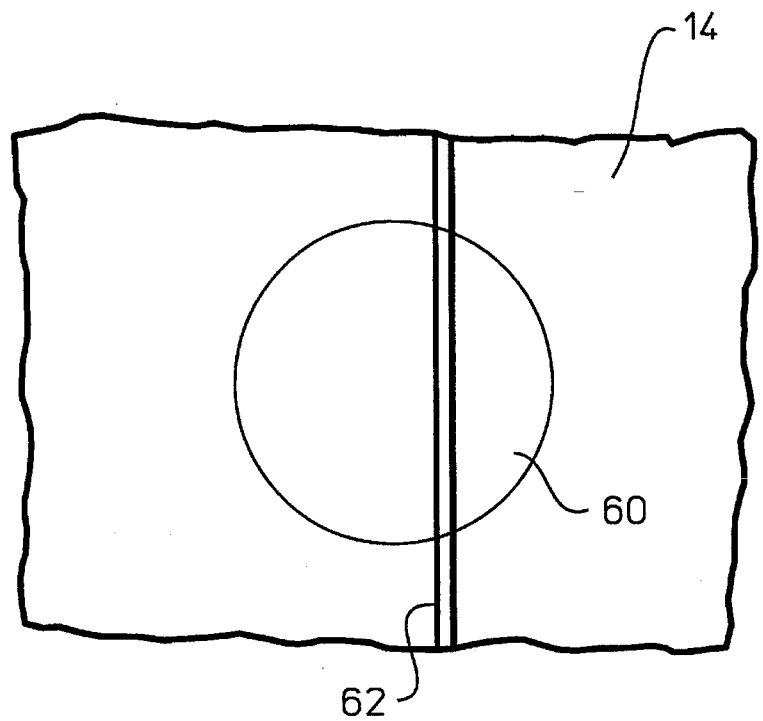
FIG. 4 shows the path of a laser beam in ionization of a sample on a membrane of the interfacing apparatus according to the present invention.

FIG. 4 shows a spot 60 of analyte deposited on a porous membrane 14. A laser beam can be swept across the surface of the porous membrane 14 so that the beam path passes through the spot 60. When the laser beam impinges on the analyte spot 60 on the porous membrane 14, the laser energy vaporizes the top layers of the matrix and the analyte (which is trapped or retained in the matrix) vaporizes. The resulting ions are then repelled and driven toward the detector 56 by the applied electrical potential.

Capillary electrophoresis systems and methods are well known in the art. For example, CE systems and methods of operation have been disclosed in U.S. Pat. No. 5,131,998 (Jorgenson et al.), U.S. Pat. No. 5,389,221 (Jorgenson et al.), U.S. Pat. No. 5,326,445 (Lauer et al.), and U.S. Pat. No. 5,302,264 (Welch et al.). These disclosures of systems and methods are incorporated by reference herein.

In general, in the CE apparatuses of the present invention, a capillary (e.g., a fused silica capillary with a polyimide coating) filled with a buffer solution is used to separate the analytes in a sample. The two ends of the capillary are immersed in two separate volumes of buffer. After introducing a sample at the inlet end of the capillary, a DC voltage (e.g., about 30 kV) is applied between the two ends of the capillary to draw the buffer through the capillary. Because of the electrical potential in the capillary, the analytes in a sample introduced in the inlet end of the capillary can be separated on the basis of their charge densities as they pass through the capillary.

Typically, the inside diameter (i.d.) of the CE capillary is about 5 μm to 200 μm. The thickness and outside diameter (o.d.) of the column are selected such that the column will have the mechanical integrity and strength appropriate for the pressure condition and manipulation during CE, as well as for withstanding repeated contact with and disengaging from the porous membrane. The selection of the dimensions (including length, i.d., o.d.) and the voltage for CE to separate particular types of analytes (e.g., antibodies) is well known in the art.

MALDI-MS equipment and methods are also know in the art. Commercial systems are available (e.g., HP G2025A MALDI-TOF from Hewlett-Packard Co., Palo Alto, Calif.). The dimensions of the metallic support can be selected depending on the shape and size of the ionization chamber in the MALDI-MS equipment. A person skilled in the art will be able to adapt the metallic support and porous membrane according to the present invention to have analytes and MALDI matrix (or matrices) deposited thereon so that they can be placed in such an equipment to conduct MALDI-MS.

EXAMPLES

Example 1

In this run, continuous elution of fluid occurred at the capillary exit end 38 and the eluted fluid was collected onto a movable XYZ surface, 12, as shown in FIG. 1. The capillary had a 75 μm i.d. and a 375 μm o.d and an overall length of 47 cm. An ultraviolet detector with absorption set to 210 nm was connected to an HP 3396 Series II Integrator with chart speed set to 0.5 cm / min. The detector was set 20 cm from the outlet end of the capillary. The collection surface, 12 was moved to a different, discrete position every 30 seconds once the elution of peaks from the exit end of the capillary had begun.

The solution in all CE injections was a 9-peptide mixture purchased from Sigma Chemical Co, (P2693—Peptide Standards for CE, St. Louis, Mo.). The mixture was prepared using Sigma Separation Buffer (Sigma, P2188, 0.1M phosphate, pH 2.5) so that the concentration of each peptide component was approximately 50 ng /μl.

A microporous polypropylene membrane, 14, obtained from 3M Corporation, (St. Paul, Minn. part number not designated) was attached to surface 12 with a spray adhesive (3M Spray Mount,#6065). The membrane was about 87 μm thick, and was treated with poly(vinyl alcohol) to be hydrophilic as described in U.S. Pat. No. 5,443,727, supra. The porous-member structure is assembled with a piece of (35 μm pores) high density porous, hydrophobic polyethylene rod that had been drilled through the center with a 0.7 mm bit. The piece was about 2.5 cm long, with a diameter of about 2 mm (obtained from Porex Technologies, Fairbum, Ga.) The reservoir above this member contained the abovementioned buffer solution that was used for the CE experiment.

Analyte solution was introduced into the capillary by electrokinetic means from a non-conducting vial at 1 kV for about 3 seconds. The sample vial was then replaced with a vial filled with buffer solution and a voltage of 10 kV was applied to execute the electrophoresis run for 20 to 30 minutes. Approximately 0.5 pmole of each analyte had entered the column. Electric current was stable throughout the CE run while fractions were collected onto the membrane. Once elution of peaks had begun, the membrane-covered surface 12 was moved to a different position every 30 seconds until the separation was completed. The surface plate was then removed from the CE and a matrix solution (0.98 μl) was added to each sample "position." The matrix solution was a 1:1 mixture of Sinapinic Acid Solution sold by Hewlett Packard (G 2055A, Palo Alto, Calif.) and 1% aqueous trifluoroacetic acid (TFA) solution. Each sample 'position' was then submitted to mass spectral analysis with a MALDI time-of-flight instrument (HPG2025, Hewlett-Packard Co., although other MALDI-MS equipment can also be used).

Figure 5:
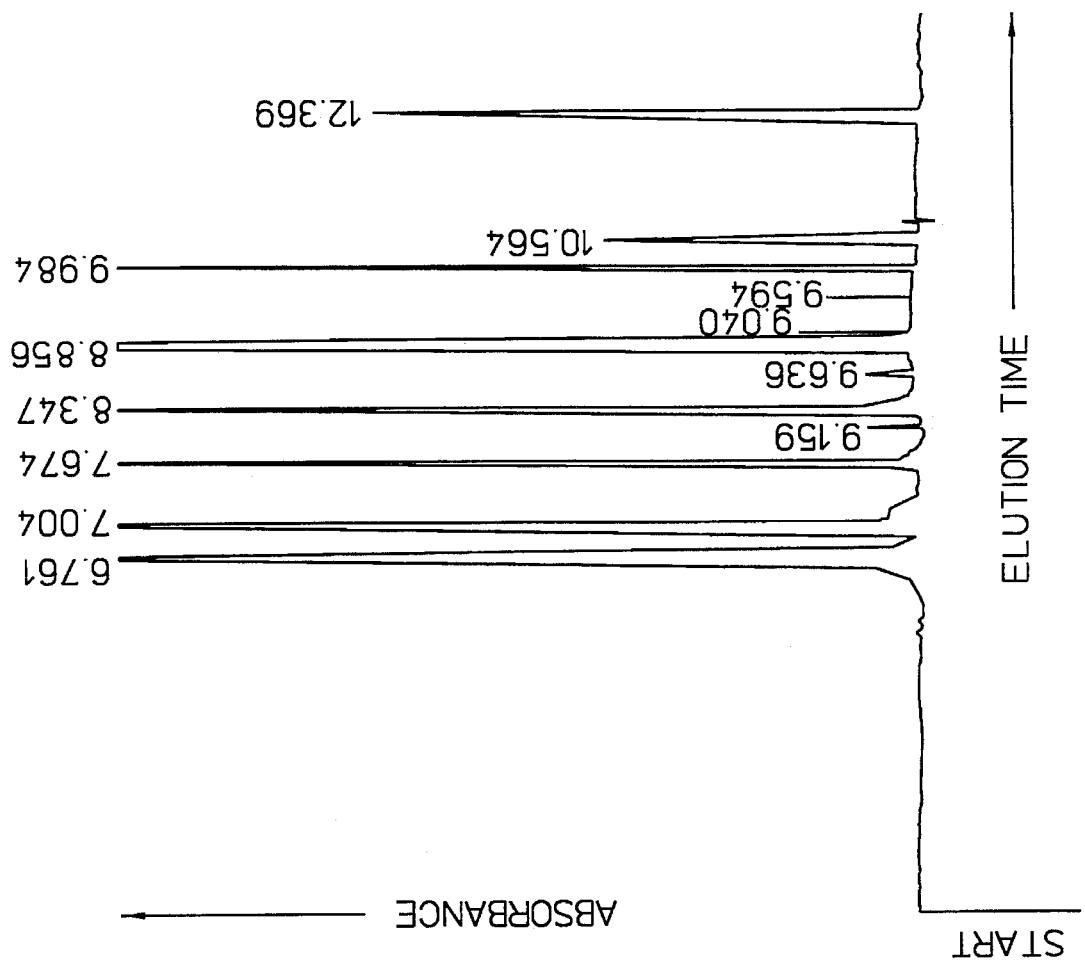
FIG. 5 is a electropherogram obtained in CE analysis of a 9-component mixture.
Figure 6B:
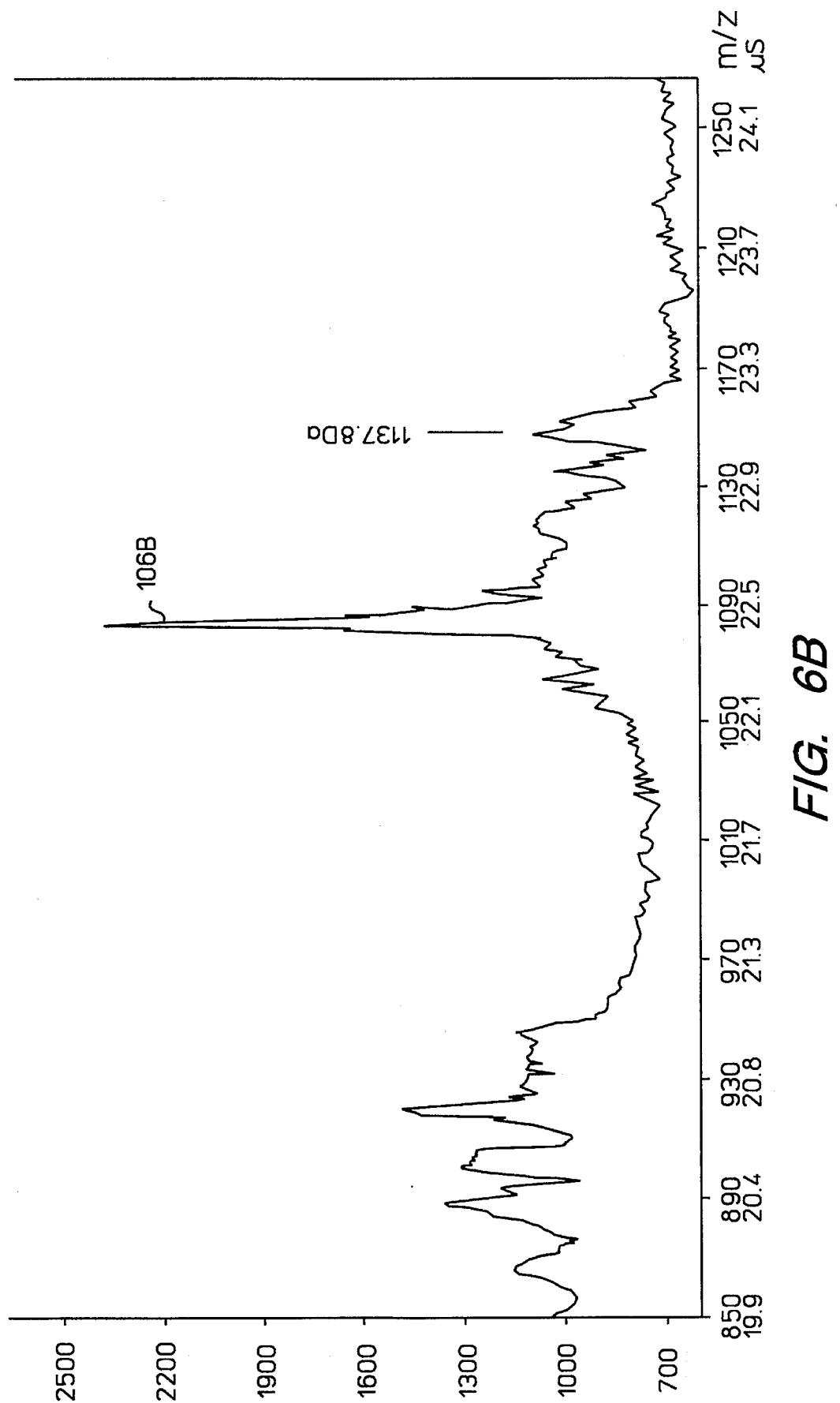
FIG. 6B shows the result of a mass spectrum showing the (Arg$^8$)-Vasopressin peak of the 9-component mixture, obtained by analyzing a CE fraction using the interfacing apparatus according to the present invention.
Figure 6C:
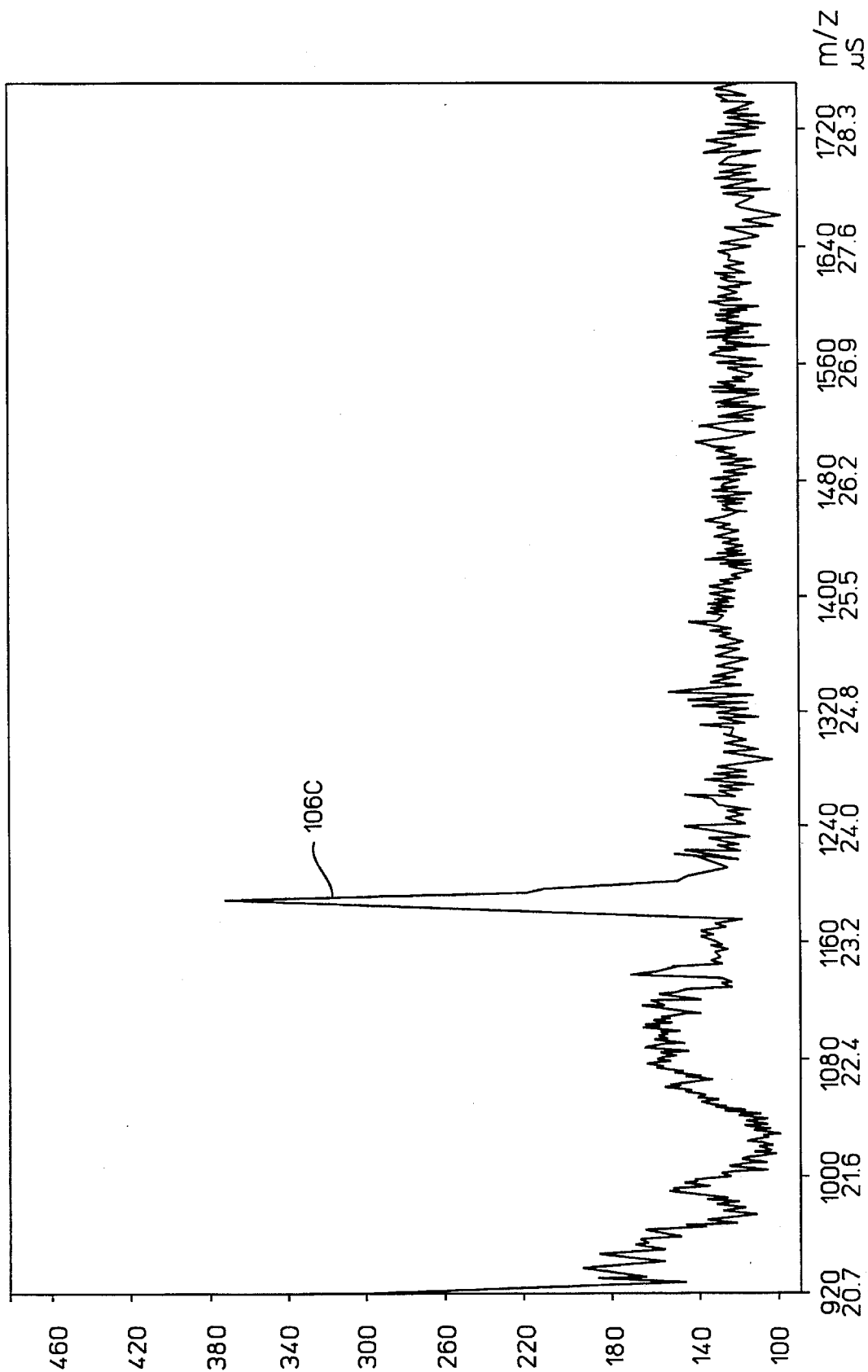
FIG. 6C shows the result of mass spectrum showing the Luteinizing Hormone Releasing Hormone peak of the 9-component mixture, obtained by analyzing a CE fraction using the interfacing apparatus according to the present invention.

FIG. 5 shows a typical electropherogram generated in CE analysis with the 9-peptide mixture injection. The peaks, in order of elution, represent Bradykinin, Bradykinin Fragment 1–5, Substance P, [Arg$^8$]-Vasopressin, Luteinizing Hormone Releasing Hormone, Bombesin, Leucine Enkephalin, Methionine Enkephalin, and Oxytocin. FIGS. 6A–D show representative mass spectra of four of the fractions in the run. The peaks 106A, 106B, 106C, 106D represent Substance P, [Arg$^8$]-Vasopressin, Luteinizing Hormone Releasing Hormone, and Bombesin, respectively. The results indicate that the interface apparatus of the present invention can be used to interface CE with MALDI-TOF mass spectrometry analysis.

Example 2

ACE run with fraction collection was executed according to the procedure of Example 1 except that membrane 14 was a microporous hydrophobic polyethylene (20 µm thick) obtained from 3M Corporation (Type 61, 3M Co., St. Paul, Minn.). In this case, the reservoir holding the porous member was filled with a 3:2 mixture of the Sigma Separation Buffer (Sigma, P2188, 0.1M phosphate, pH 2.5) and acetonitrile (Aldrich Chemicals Co, #27,071-7, Milwaukee, Wis.). The CE separation and collection of eluents occurred as in Example 1 and the results showed that the fractions could be submitted for MALDI-TOF mass spectrometry analysis as stated above.

Although the illustrative embodiments of the apparatus and method according to the present invention have been described in detail, it is to be understood that the above-described embodiments can be modified by one skilled in the art, especially in sizes and shapes and combination of various described features without departing from the spirit and scope of the invention.

What is claimed is:

1. An apparatus for collecting analyte samples from capillary electrophoresis (CE) for matrix-assisted laser desorption ionization (MALDI) mass spectrometry (MS), comprising:
   (a) capillary, having an inlet end and an exit end, for conducting analyte and fluid during CE;
   (b) metallic support for supporting a porous membrane such that the porous membrane can substantially contact the capillary exit end during CE, the metallic support being suitable for placing with the porous membrane in a mass spectrometer to act as a repeller for MALDI;
   (c) porous member having at least a portion thereof contacting and being generally concentric with the capillary exit end, the porous member and the capillary exit end being adapted to enable substantially contacting the porous membrane during CE, and being adapted to separate the capillary exit end from the porous membrane for repositioning such that the capillary exit end substantially contacts the porous membrane at a different location to deposit noncontinuously different fractions of the sample, the porous member being capable of conducting electricity in the presence of an electrolyte; and
   (d) power supply for applying an electrical potential between the porous member and the inlet end of the capillary to drive analyte through the capillary during capillary electrophoresis when an electrolyte provides electrical communication between the capillary exit end and the porous member.

2. The apparatus according to claim I further comprising the porous membrane, wherein the porous membrane has a surface adapted to hold a MALDI matrix and elution fractions from CE.

3. The apparatus according to claim 2 wherein the matrix is selected from the group consisting of nicotinic acid, 2,5-dihydroxybenzoic acid, sinapinic acid, succinic acid, glycerol, α-cyano-4-hydroxycinnamic acid, and 3-hydroxypicolinic acid.

4. The apparatus according to claim 2 wherein the porous membrane is a hydrophilic polymeric membrane.

5. The apparatus according to claim 4 wherein the hydrophilic polymeric membrane is a polyolefin membrane.

6. The apparatus according to claim 4 wherein the hydrophilic polymeric membrane is made of polypropylene or polyethylene.

7. The apparatus according to claim 1 wherein the porous member and the capillary exit end both substantially contact a common surface of the porous membrane during capillary electrophoresis.

8. The apparatus according to claim 1 further comprising a reservoir in fluid communication with the porous member to supply the electrolyte thereto.

9. The apparatus according to claim 1 wherein the metallic support is a metallic plate.

10. A method for interfacing capillary electrophoresis (CE) and matrix-assisted laser desorption ionization (MALDI) mass spectrometry (MS) for analysis of a sample suspected of containing analyte, comprising:
    substantially contacting a porous membrane with a porous member and with an exit end of a capillary to provide fluid communication via an electrolyte such that during CE an electrical potential can be implemented between an inlet end of the capillary and the porous member to deposit fractions of the sample noncontinuously on different areas of the porous membrane by lifting the capillary exit end and the porous member from the porous membrane and repositioning on the porous membrane at a different location to deposit different fractions of the sample exiting the capillary, at least a portion of the porous member is generally concentric with the capillary exit end, such that the porous membrane with the fractions deposited thereon can be processed and placed in a mass spectrometer for MALDI to analyze the sample.

11. The method according to claim 10 further comprising supporting the porous membrane during CE with a metallic support such that the porous membrane and the metallic support can be put in a mass spectrometer for MALDI so that the metallic support will act as a repeller.

12. The method according to claim 11 wherein the MALDI matrix further comprising: placing the porous membrane and the metallic support in a mass spectrometer, such that the metallic support acts as a repeller for MALDI in MS.

13. The method according to claim 10 wherein a MALDI matrix is applied on the fractions after the fractions are deposited on the porous membrane.

14. The method according to claim 10 wherein the capillary exit end is inserted through the porous member.

15. The method according to claim 10 wherein a matrix selected from the group consisting of nicotinic acid, 2,5- dihydroxybenzoic acid, sinapinic acid, succinic acid, glycerol, α-cyano-4-hydroxycinnamic acid, and 3-hydroxypicolinic acid is deposited on the porous membrane.

16. The method according to claim 10 wherein a hydrophilic polymeric membrane is used for the porous membrane.

17. The method according to claim 10 wherein a hydrophilic polypropylene or polyethylene porous membrane is used for the porous membrane.

18. A method for interfacing capillary electrophoresis (CE) and matrix-assisted laser desorption ionization (MALDI) mass spectrometry (MS), comprising:

positioning a porous member and an exit end of a capillary for CE proximate thereto noncontinuously on a porous membrane supported with a metallic support such that at least a portion of the porous member is generally concentric with the exit end of the capillary, the porous member and the capillary exit end substantially contacting the porous membrane noncontinuously while eluting the sample during CE through the capillary, the elution being effected by contacting the capillary exit end and the porous member with an electrolyte and implementing an electrical potential between an inlet end of the capillary and the porous member, said substantially noncontinuously contact being implemented by lifting the capillary exit end and the porous member from the porous membrane and repositioning on the porous membrane at a different location, thereby depositing fractions of the sample on different areas of the porous membrane such that the porous membrane with CE eluents deposited thereon is suitable for MALDI-MS.

19. A method of making an apparatus for collecting fractions from capillary electrophoresis (CE) for matrix-assisted laser desorption ionization (MALDI) mass spectrometry (MS), comprising:

(a) inserting a CE capillary that has an inlet end and an exit end into a porous member such that at least a portion thereof is generally concentric to the exit end of the capillary and the exit end is about flush with a surface of said portion of the porous member, for elution of CE analytes during capillary electrophoresis;

(b) positioning a metallic support proximate the exit end of capillary, for supporting a porous membrane such that the porous membrane substantially contacts the capillary exit end during capillary electrophoresis, the metallic support being suitable for placing with the porous membrane in a mass spectrometer to act as a repeller for MALDI, the capillary exit end and the metallic support being adapted to separate the capillary exit end from the porous membrane and reposition on the porous membrane at a different location to deposit noncontinuously different fractions of fluid exiting the capillary on the porous membrane during CE; and (c) providing a power supply suitable for applying an electrical potential between the porous member and the inlet end of the capillary to drive the CE analytes through the capillary during CE when an electrolyte provides electrical communication between the capillary exit end and the porous member.

* * * * *